United States Patent [19]
Chartrain et al.

[11] Patent Number: 5,871,981
[45] Date of Patent: Feb. 16, 1999

[54] **CONVERSION OF INDENE TO (1S)-AMINO-(2R)-INDANOL FREE OF ANY STEROISOMER BY COMBINATION OF FERMENTATION OF *RHODOCOCCUS SP.* ATCC 55805 AND CHEMICAL STEPS**

[75] Inventors: Michel Chartrain, Westfield; Barbara A. Jackey, Bloomfield; Brian Heimbuch, North Burnswick, all of N.J.; Colleen S. Taylor, Folsom, Calif.

[73] Assignee: Merck & Co., Inc., Rahway, N.Y.

[21] Appl. No.: 909,867

[22] Filed: Aug. 12, 1997

Related U.S. Application Data

[60] Provisional application No. 60/023,944 Aug. 14, 1996.
[51] Int. Cl.$^6$ ............... C12P 7/02; C12N 1/20; B01D 15/00; C07C 7/00
[52] U.S. Cl. .............. 435/155; 435/252.2; 585/812; 210/660
[58] Field of Search ................ 435/155, 189, 435/190, 191, 192, 252.2, 803; 568/700, 704, 705, 715; 585/825, 812; 210/656, 660

[56] References Cited

U.S. PATENT DOCUMENTS

| | | | |
|---|---|---|---|
| 5,420,353 | 5/1995 | Verhoeven et al. | 564/399 |
| 5,449,830 | 9/1995 | Verhoeven et al. | 564/400 |
| 5,605,819 | 2/1997 | Chartrain et al. | 435/123 |
| 5,648,534 | 7/1997 | Igarashi et al. | 564/130 |

FOREIGN PATENT DOCUMENTS

| | | |
|---|---|---|
| 0 098 137 A2 | 1/1984 | European Pat. Off. . |
| WO 95/24374 | 9/1995 | WIPO . |
| WO96/12818 | 5/1996 | WIPO . |

OTHER PUBLICATIONS

Gibson et al, "Desaturation, dioxygenation, and monooxygenation reactions catalyzed by naphthalene dioxygenase from Pseudomonas sp. strain 9816–4", Chemical Abstrats, vol. 123, Abs. No. 50834 (1995).

Bezborodov et al., "News Strain of Rhodococcus erythropolis bacteria", 1993, WPI No. 93–318308 (Title Only of SU 1752767).

Wackett et al., "Benzylic Monooxygenation Catalyzed by Toluene Dioxygenase from Pseudomonas putida", Biochemistry, vol. 27, pp. 1360–1366 (1988).

Gibson et al. "Desaturation, dioxygenation and monooxygenation reactions catalyzed by naphthalene dioxygenase from Pseudomonas sp. strain 9186–4," J. Bacteriol. (May 1995) 177(10):2615–21, May 1995.

*Primary Examiner*—Jon P. Weber
*Assistant Examiner*—Susan Hanley
*Attorney, Agent, or Firm*—Kenneth R. Walton; Melvin Winokur

[57] ABSTRACT

A method for preparing (1S)-amino-(2R)-indandiol substantially free of its stereoisomers is presented. The method comprises culturing indene with Rhodococcus sp. ATCC 55805, recovering the indandiol and subjecting the indandiol to chiral specific crystallization, treatment with strong acid and reverse ion pair extraction.

6 Claims, No Drawings

CONVERSION OF INDENE TO (1S)-AMINO-(2R)-INDANOL FREE OF ANY STEROISOMER BY COMBINATION OF FERMENTATION OF *RHODOCOCCUS SP.* ATCC 55805 AND CHEMICAL STEPS

BACKGROUND OF THE INVENTION

The present application is related to U.S. Pat. No. 60/023,944, filed Aug. 14, 1996, the content of which is hereby incorporated by reference.

The present invention is concerned with a process for synthesizing intermediates for compounds which inhibit the protease encoded by human immunodeficiency virus (HIV), and in particular certain oligopeptide analogs, such as Compound J in the Examples below. These compounds are of value in the prevention of infection by HIV, the treatment of infection by HIV and the treatment of the resulting acquired immune deficiency syndrome (AIDS). These compounds are also useful for inhibiting renin and other proteases.

The inventions described herein concern the conversion of indene to (2S)-amino-(1R)-indanol as illustrated by the following Scheme I.

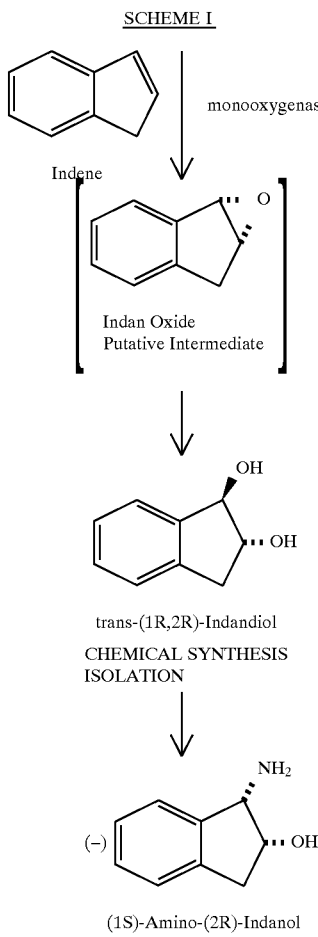

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature*, 313, 277 (1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et al., *Science*, 231, 1567 (1986); Pearl, L. H. et al., *Nature*, 329, 351 (1987)]. The end product compounds, including certain oligopeptide analogs that can be made from the novel intermediates and processes of this invention, are inhibitors of HIV protease, and are disclosed in EPO 541,168, which published on May 12, 1993. See, for example, Compound J therein, also illustrated in the Examples below.

The present application discloses an improved process to make, in substantial stereoisomeric purity, 1 (S)-amino-2(R)-hydroxy indan of the structure

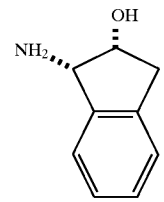

which is a sidechain group of Compound J, which is a potent inhibitor of HIV protease.

Previous attempts at synthesis involve inefficient production of the racemate 1 (±)-amino-2(±) hydroxy indan from the racemic indene oxide. Other attempts at synthesis involve bioconversion of indene with a fungal haloperoxidase to give predominantly trans-(2S, 1 S)-bromoindanol, which is then subjected to various chemical steps to give (1S)-amino-(2R)-indanol. Another bioconversion process involves contacting toluene dioxygenase with indene to give a cis-indandiol, which by chemical process affords (1S)-amino-(2R)-indanol. Still other attempts at synthesis relate to chemical synthesis with racemic epoxidation as an intermediate step, followed by resolution with L-tartaric acid.

The present invention provides needed improved alternatives. In the processes of the present invention, the tartaric acid resolution step is eliminated by combining stereoselective bio-oxidation of substrate indene to trans -(1 (R),2R)-indandiol. Further chemical treatment gives (1S)-amino-(2R)-indandiol, e.g. treatment with a nitrile in the presence of aqueous acid according to the Ritter reaction, followed by either reverse ion pair extraction or cation exchange chromatography.

In the processes of the present invention, indene is converted by the action of the enzyme monooxygenase (and perhaps other enzymatic activities, e.g., epoxide hydrolase) to a mixture of trans indandiols containing predominantly the desired (1R,2R) stereoisomer. The desired (1R,2R) stereoisomer is isolated using purification steps, e.g., adsorption, extraction, crystallization to yield substantially pure crystallized trans(1R,2R)-indandiol.

An enantiomeric excess of over about 99% (from indene to the substantially pure trans-(1R,2R)-indandiol) is typical of the processes of the present invention.

BRIEF DESCRIPTION OF THE INVENTION

The present invention provides new methods to effect the synthesis of trans-(1R,2R) indandiol, by bioconversion by the action of the enzyme monooxygenase. The intracellular expression of monooxygenase is probably induced by indene. Subsequent chemical steps permit formation of (1S)-amino-(2R)-indanol, another intermediate. These product compounds are intermediates for compounds useful in the synthesis of inhibitors of HIV protease, renin and other proteases, e.g., Compound J.

DETAILED DESCRIPTION OF THE INVENTION

The present invention is concerned with a process for synthesizing intermediates for compounds which inhibit the HIV protease. One desired intermediate is (1S)-amino-(2R)-indanol substantially free of its undesired stereoisomers. Another desired intermediate is (1R,2R)-indandiol substantially free of its undesired stereoisomer (1S,2S)-indandiol.

The present invention relates to a process for synthesizing (1R,2R)-indandiol, comprising the steps of:
 a) contacting a quantity of monooxygenase with a quantity of indene;
 b) incubating the resulting mixture;
 c) to give (1R,2R)-indandiol.

One embodiment of the present invention is the process for synthesizing (1R,2R)-indandiol substantially free of any stereoisomer, comprising the steps of:
 a) contacting a quantity of monooxygenase with a quantity of indene;
 b) incubating the resulting mixture;
 c) purifying (1R,2R)-indandiol;
 d) subjecting the product of Step (c) to crystallization;
 e) to give (1R,2R)-indandiol substantially free of any stereoisomer.

Another embodiment of the present invention is the process for synthesizing (1S)-amino-(2R)-indanol substantially free of any stereoisomer, comprising the steps of:
 a) contacting a quantity of monooxygenase with a quantity of indene;
 b) incubating the resulting mixture;
 c) purifying (1R,2R)-indandiol;
 d) subjecting the product of Step (c) to crystallization;
 e) to give (1R,2R)-indandiol substantially free of any stereoisomer;
 f) dissolving one equivalent of the (1R,2R)-indandiol of step (e) in excess acetonitrile to give a second mixture, and maintaining the second mixture between about –40° C. and about 25° C.;
 g) mixing thereto excess equivalents of strong acid, and maintaining the reaction at between about –40° C. and about 25° C.;
 h) to give (1S)-amino-(2R)-indanol substantially free of any stereoisomer.

A pure culture of Rhodococcus sp. MA7205, ATCC 55805 is also disclosed. A sample of this culture was deposited with the ATCC on Aug. 13, 1996.

One variation in the processes of the present invention is the process of the the present invention, further comprising the additional steps of i) subjecting the product of step (h) to reverse ion pair extraction;
 j) to give substantially pure (1S)-amino-(2R)-indanol.

Another variation in the processes of the present invention is the process of the present invention, further comprising the additional steps of
 i) subjecting the product of step (h) to cation exchange chromatography;
 j) to give substantially pure (1S)-amino-(2R)-indanol.

Also encompassed in the present invention are the processes of the present invention, wherein the monoxygenase is from Rhodococcus sp. MA7205 (I24), ATCC 55805.

In the bioconversion of indene to a mixture of trans-(1R, 2R)-indandiol and trans-(1S,2S)-indandiol, any microbe that carries out the biotransformation is suitable. Preferred microbes include those giving substantial stereoisomeric excess of the (1R,2R) stereoisomer, e.g., naphthalene dependent microbes or naphthalene independent microbes. Applicants have isolated a naphthalene independent Rhodococcus sp. strain I 24, which expresses the monooxygenase enzyme and perhaps epoxide hydrolase. Such strain eliminates the process steps for naphthalene induction of the enzyme.

Fermentation of indene with a microorganism containing monooxygenase, and optionally epoxide hydrolase, is conducted in the presence of an oil reservoir for the indene, e.g., silicone oil. The oil reservoir for indene avoids the toxicity to cells of high concentrations of indene. The preferred microorganism for such fermentations is Rhodococcus sp. strain I 24, most preferably ATCC 55805. Other suitable microorganisms include other Rhodococci, and E. coli transformed with genes for the relevant enzymes.

After fermentation, the fermentation mixture is spun down or centrifuged to give three layers. There is a top layer of the oil reservoir, typically silicone oil, then a middle aqueous layer with the desired indandiol bioconverted products, and a bottom layer of cells and debris. The middle layer is subjected to further treatment.

The middle aqueous layer is then mixed with a hydrophobic resin to bind the indandiol products. Suitable hydrophobic resins include, but are not limited to, styrene-divinyl benzene resin, reverse phase C18 resin, or uncharged acrylic resins.

After washing the resin with water or other suitable aqueous solvent, the resin is eluted to remove bound indandiol with eluting solvent. Eluting solvents include any organic solvent, preferably a mixture of methanol and water, most preferably a mixture of about 40%(v/v) methanol and about 60%(v/v) water. The eluting solvent must be inmmiscible with the extraction solvent for crystallization. Crystallization of trans-indanol is carried out by gradually lowering the temperature from about 25° C. to about 10° C., with stirring until crystals are formed.

ATCC Deposits

Before the U.S. filing date of the present application, a sample of the microorganism I 24 was deposited at the American Type Culture Collection (ATCC), 10801 University Boulevard, Manassas, Va. 20110-2209 The culture access designation is ATCC 55805. This deposit will be maintained in the ATCC for at least 30 years and will be made available to the public upon the grant of a patent disclosing it. It will be understood that the availability of a deposit does not constitute a license to practice the subject invention in derogation of patent rights granted by government action.

General Characteristics of ATCC 55805

The physical characteristics and taxonomy, including morphological, cultural, biological and physiological characteristics are briefly described hereinbelow.

I 24—ATCC 55805 MA7205 Non-motile, Gram positive, pleomorphic filaments [width 1.14μ, average length ~7.6μ at 48 hours]. Vegetative mycelia are extensively branched at the middle of the growth cycle (24–48 hours), but after 72 hours the culture fragments into pleomorphic cocci. Aerial mycelia are not produced. Endospores are not produced. Mesophilic, with growth occurring at 28° C. and 37° C. The diamino acid in the cell wall is meso diamino pimelic acid. Arabinose, galactose, glucose, and rhamnose are found in the cell wall. Strictly aerobic, catalase positive, and oxidase negative. On trypticase soy agar colonies are 1–1.5 mm in diameter, orange in color, opaque, convex, and have an entire edge. The surface is matte and the texture is pasty. No diffusible pigments are produced. The major fatty acids are 16:0 and 18:1w9c. Also present in smaller amounts are tuberculostearic acid and a variety of monounsaturated and straight chain fatty acids. Comparison of the fatty acid profile of MA7205 with other actinomycetes showed a high similarity to mycolic acid containing strains of Rhodococcus and Nocardia. Based upon the combined results, we have placed MA7205 into the genus Rhodococcus.

General Description Of Culture Conditions

The preferred source of carbon in the nutrient medium are carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates, and yeast hydrolysates, corn steep liquor, dried yeast, wheat germ, feather meal, peanut powder, distiller's solubles, etc., as well as inorganic and organic nitrogen compounds such as ammonium salts (e.g., ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

As to the conditions for the production of cells in massive amounts, submerged aerobic cultivation conditions are preferred. For the production in small amounts, a shaking culture in a flask is employed. Furthermore, when the growth is carried out in large tanks, it is desirable first to produce an inoculum of the organism by inoculating a relatively small quantity of culture medium with the organism stored at −20° to −70° C. and culturing said inoculated medium, also called the "seed medium", and then to transfer the resulting inoculum aseptically to large tanks. The fermentation medium, in which the inoculum is produced, is generally autoclaved to sterilize the medium prior to inoculation. The pH of the medium is generally adjusted to about 7.0 prior to the autoclaving step.

Agitation and aeration of the culture mixture may be accomplished in a variety of ways. Agitation may be provided by impeller or similar mechanical agitation equipment, shake flask bioreactor, by various pumping equipment or by the passage of sterile air through the medium. Aeration may be effected by passing sterile air through the fermentation mixture.

The fermentation is usually conducted at a temperature between about 25° C. and 37° C., preferably 30° C., for a period of about 0.5 to 5 days, preferably 2, which may be varied according to fermentation conditions and scales. Preferably, the production cultures are incubated for about 2 days at 30° C. in a stirred bioreactor operating at an impeller speed of about 300 rpm.

Preferred culturing/production media for carrying out the fermentation include the following media:

Medium A composition for indene bioconversion by Rhodococcus sp. I 24: medium contains (per liter of water): $(NH_4)_2SO_4$, 0.66 g; $MgSO_4.7H_2O$: 1.0 g; $CaCl_2.2H_2O$, 0.015 g; trace element solution A, 1.0 ml; stock solution A, 1.0 ml, 1.0M Phosphate buffer, 20 ml. The trace element solution A contains (per liter of water): $FeSO_4.7H_2O$, 0.5 g; $ZnSO_4.7H_2O$, 0.4 g; $MnSO_4.H_2O$, 0.02 g, $H_3BO_3$, 0.015 g; $NiCl_2.6H_2O$, 0.01 g; EDTA 0.25 g; $CoCl_2.6H_2O$, 0.05 g; $CuCl_2.2H_2O$, 0.005 g. Stock A solution is made up of: (per liter of water) $NaMoO_4.2H_2O$, 2.0 g; FeNa.EDTA, 5.0 g. Phosphate buffer (1M) contains (per liter of water): $K_2HPO_4$, 113 g; $KH_2PO_4$, 47 g.

Further Steps After Fermentation

Silicone Oil Removal

The whole broth is transferred from the fermentor to a harvest tank and allowed to settle a minimum of 4 hours. Usually settling is done overnight. After settling, the lower aqueous phase containing the trans-indandiol and fermentation solids is transferred to the column feed tank. The upper organic layer is discarded.

The resulting aqueous layer can be further treated, e.g. filtration or adsorption on a brominated styrene divinyl resin bed. Alternatively and preferably, the aqueous layer is subjected to extraction without further manipulations after removal of upper organic layer.

An equal volume of isopropyl acetate is added directly to the unconcentrated aqueous phase and agitated for a minimum of 5 minutes. The phases are then settled by gravity for a minimum of 2 hours. The upper organic phase is removed and then the lower aqueous phase is extracted three more times with an equal volume of isopropyl acetate.

Product Recovery

The product trans (1R,2R) indandiol is found in the aqueous phase of the media, and accordingly can be isolated and purified by conventional methods such as centrifugal or gravitational clarification of the aqueous phase, concentration under reduced pressure, extraction with a conventional solvent, such as isopropyl acetate and the like, pH adjustment, treatment with a conventional resin (e.g., anion or cation exchange resin, non-ionic resin, etc.), treatment with a conventional adsorbent (e.g., activated charcoal, silica gel, cellolose, alumina, etc.), crystallization, recrystallization, and the like.

The preferred sequence of methods includes aqueous phase clarification, solvent extraction of product, solvent concentration under reduced pressure, an crystallization.

Conversion of trans-(1R,2R)-Indandiol to cis-(1S)-Amino-2R-Indanol

Reaction of the trans-(1R,2R)-indandiol with acetonitrile, followed by hydrolysis in the presence of water, is carried out rapidly. One equivalent of solid trans-(1R,2R)-indandiol is dissolved in excess acetonitrile, with or without organic solvent. A typical solvent is dichloromethane. The mixing of the diol with acetonitrile is exothermic, so cooling is typically carried out before contacting with strong acid.

The mixture of trans-(1R,2R)-indandiol and acetonitrile is then contacted with excess equivalents of strong acid, such as triflic acid, methanesulfonic acid or sulfuric acid. Typically about two equivalents of strong acid are added. After about one or two hours, excess water equivalents are added. The remaining acetonitrile is removed by distillation or refluxing, to give a Ritter solution.

The resulting cis-(1S)-amino-(2R)-indanol is substantially free of the stereoisomer trans-aminoindanol. Typically, resolution is not needed in subsequent steps.

Purification of cis-(1S)-amino-(2R)-indanol

The Ritter solution then may be subjected to various treatments to remove acid contaminants.

A. Reverse Ion Pair Extraction

Base is added to neutralize the acid, then to raise the pH to about 12 or higher, to give a basified Ritter solution. This basified Ritter solution is extracted with any organic solvent having a suitable solubility for cis-aminoindanol; e.g. methylene chloride, ethyl acetate or 1-butanol, preferably 1-butanol. The aqueous layer(s) then may be discarded.

To the organic layer(s) containing cis-aminoindanol is added a suitable acid in excess of cis-aminoindanol equivalents. Suitable acids will form a salt complex with cis-aminoindanol and make the cis-aminoindanol more soluble in aqueous solution. Such suitable acids include but are not limited to L-tartaric, D-tartaric, meso-tartaric, ascorbic, malonic, citric, formic acids, HCl, preferably L-tartaric acid.

The resulting salt in organic solvent is then extracted with an aqueous solution, e.g. water, to give an aqueous extract. Titration of base equivalents into the aqueous extract will give crystallization beginning at about pH 8–9. Crystallization is typically complete before titration with base reaches pH of about 11–12. The resulting. (1S)-amino-(2R)-indanol is substantially pure.

B. Cation Exchange Chromatography

Alternatively, the Ritter solution may be subjected to cation exchange chromatography to remove acid contaminants. Any cation exchange resin is suitable, but typically comprises styrene-divinylbenzene resin, attached thereto with acid groups, such as sulfonic acid or carboxylic acid.

The resin is mixed with the Ritter solution, then washed with water or other aqueous solvent to remove unwanted acid. The bound cis-aminoindanol is eluted by the steps of adding base (to increase pH to keep cis-aminoindanol soluble), followed by elution with any one of a variety of solvents, e.g. methanol, acetonitrile or THF in water. The basification-elution cycle may be repeated several times to quantitatively elute cis-aminoindanol off the resin. The resulting (1S)-amino-(2R)-indanol is substantially pure.

Formulations

The product compounds synthesized from the intermediates of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The processes and intermediates of this invention are useful for the preparation of end-product compounds that are useful in the inhibition of HIV protease, the prevention or treatment of infection by the human immunodeficiency virus (HIV), and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the end-product compounds that can be made from the processes and intermediates of this invention are useful in treating infection by HIV after suspected past exposure to HIV by, e.g., blood transfusion, organ transplant, exchange of body fluids, bites, accidental needle stick, or exposure to patient blood during surgery.

The end-product HIV protease inhibitors are also useful in the preparation and execution of screening assays for antiviral compounds, including their use as controls. For example, end-product compounds are useful for isolating enzyme mutants, which are excellent screening tools for more powerful antiviral compounds. Furthermore, such compounds are useful in establishing or determining the binding site of other antivirals to HIV protease, e.g., by competitive inhibition. Thus the end-product compounds that are made from the processes and intermediates of this invention are commercial products to be sold for these purposes.

The end product HIV protease inhibitor Compound J has the structure

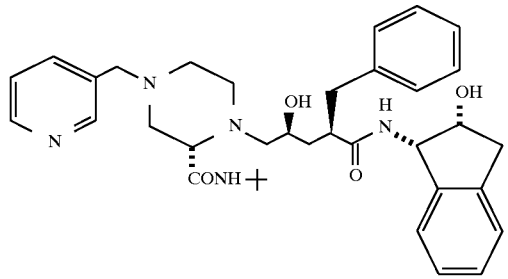

or pharmaceutically acceptable salts or hydrates thereof. Compound J is named
N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide;
[1S-[1a[aS*,gR*,d(R*)],2a]]-N-(2,3-dihydro-2-hydroxy-1H-inden-1 -yl)-2-[[(1,1-dimethylethyl)amino]carbonyl]-g-hydroxy-a-(phenyl-methyl)-4-(3-pyridinylmethyl)-2-piperazinepentaneadmide; or
N-(1(S)-2,3-dihydro-2(R)-hydroxy-1H-indenyl)-4(S)-hydroxy-2(R)-phenylmethyl-5-[4-(3-pyridylmethyl)-2(S)-t-butylcarbamoyl)-piperazinyl]pentaneamide.

HIV protease inhibitor compounds that can be made from the intermediates and processes of the instant invention are disclosed in EPO 541,168. The HIV protease inhibitory compounds may be administered to patients in need of such treatment in pharmaceutical compositions comprising a pharmaceutical carrier and therapeutically-effective amounts of the compound or a pharmaceutically acceptable salt thereof. EPO 541,168 discloses suitable pharmaceutical formulations, administration routes, salt forms and dosages for the compounds.

The compounds of the present invention, may have asymmetric centers and occur as racemates, racemic mixtures and as individual diastereomers, or stereoisomers with all isomeric forms being included in the present invention. A mixture of stereoisomers includes a 1:1 mixture, as well as any other mixture, e.g., 1:4, 4:3, 2:1.

Representative experimental procedures utilizing the novel process are detailed below. These procedures are exemplary only and are not limitations on the novel process of this invention.

EXAMPLE 1

Isolation of naphthalene degrading microorganisms

An amount of about 1 gram of a soil or sludge sample was placed into a 250 ml-Erlenmeyer flask containing 25 ml of medium A supplemented with 0.01% yeast extract and 5 ml of silicone oil. Medium A contains (per liter of water): $(NH_4)_2SO_4$, 0.66 g; $MgSO_4.7H_2O$: 1.0 g; $CaCl_2.2H_2O$, 0.015 g; trace element solution A, 1.0 ml; stock solution A, 1.0 ml, 1.0M Phosphate buffer, 20 ml. The trace element solution A contains (per liter of water): $FeSO_4.7H_2O$, 0.5 g; $ZnSO_4.7H_2O$, 0.4 g; $MnSO_4.H_2O$, 0.02 g, $H_3BO_3$, 0.015 g; $NiCl_2.6H_2O$, 0.01 g; EDTA, 0.25 g; $CoCl_2.6H_2O$, 0.05 g; $CuCl_2.2H_2O$, 0.005 g. Stock A solution is made up of: (per liter of water) $NaMoO_4.2H_2O$, 2.0 g; FeNa.EDTA, 5.0 g. Phosphate buffer (1M) contains (per liter of water): $K_2HPO_4$, 113 g; $KH_2PO_4$, 47 g. Naphthalene was supplied as solid flakes (3 to 5) to the medium. After 3 days of incubation at 28° C. on a shaker top operated at 220 revolutions per minute, an amount of 2 ml of the primary enrichment culture was transferred to a 250 ml Erlenmeyer flask containing 25 ml of medium A, 5 ml of silicone oil and flakes of naphthalene (3 to 5). After 72 hours of incubation under the same conditions as described above, a 1 ml aliquot of the culture was inoculated into a 250-ml Erlenmeyer flask containing 25 ml of medium A, 5 ml of silicone oil and naphthalene flakes (3 to 5). This third stage enrichment flask was incubated under the same conditions described above. After 72 hours, aliquots of the culture contained in these third stage enrichment flasks were plated onto medium A agar plates. Naphthalene, the sole carbon source, was delivered in the vapor phase by placing a flake in the center of each Petri dish. The Petri dishes were placed in heat-sealable pouches. The sealed pouches were incubated for up to 7 days at 28° C. After that incubation period, microbial colonies were picked and transferred to new medium A plates. These plates were incubated under the same conditions as described above. From each plate, an isolated colony was picked and transferred into a glass tube containing 5 ml of tryptic soy broth. The tubes were placed into a 30° C. incubator for 3–4 days after which, microbial growth was visible in most tubes. The microbial cultures contained in these tubes (1 ml) were used to inoculate 250-ml Erlenmeyer flasks containing 25 ml of medium K, 5 ml of sterile silicone oil, several (4 to 5) flakes of naphthalene, and 150 μl of indene. Medium K contains (per liter of water): Glucose, 20 g; glycerol, 20 g; yeast extract, 3 g; $FeSO_4.7H_2O$, 0.1 g; $K_2HPO_4$, 2 g; $(NH_4)2.SO_4$, 1 g; $MgSO_4.7H_2O$, 0.1 g; MOPS, 20 g, A9 solution, 2.5 ml. The pH of the medium is adjusted to 7.2 prior to autoclaving. A9 solution contains (per liter of water): $HBO_3$, 0.3 g; $ZnCL_2$, 0.05 g, $MnCl_2.4H_2O$, 0.03; $CoCl_2$, 0.2 g; $CuCl_2.2H_2O$, 0.01 g; $NiCl_2.6H_2O$, 0.02; $NaMoO_{4.2}H_2O$, 0.03 g. The flasks were incubated at 30° C. on a shaker operated at 220 revolutions per minute. After 4 days of incubation, a 1 ml aliquot of these cultures was mixed was an equal amount of isopropyl alcohol and centrifuged. The resulting supernatant was filtered and the presence of indandiol was detected using a reverse phase HPLC system.

The HPLC system was equipped with a column (diisopropyl n-octyl bromide bound to silical) (4.6 mm×25 cm) and separation was achieved with a gradient-based elution employing a mobile phase comprised of acetonitrile and buffered water (10 mM $KH_2PO_4$) delivered at a flow rate of 1.0 ml/min. The amount of acetonitrile delivered was linearly increased from 10% to 40% over 15 minutes. Detection was performed at 220 nm at 22° C. Under these conditions, trans-indandiol and cis-indandiol eluted after 9.8 and 10.2 minutes respectively. Chirality of the trans-indandiol and cis-indandiol was determined as follows. An aliquot of the culture was centrifuged, and the supernatant was mixed with an equal volume of ethyl acetate. The solvent layer was evaporated under a nitrogen stream, and the residues were resuspened in methanol. The filtered methanol solution was then injected into a supercritical fluid HPLC. A flow of 0.98 ml/minute of liquid carbon dioxide and 0.02 ml/minute of methanol delivered to a column (amylose tris(3,5-dimethylphenyl carbamate on silical-gel) achieved the separation of the 2 trans-indandiols (1R,2R and 1S,2S after 98 min and 95 min respectively) at 30° C. Detection was performed at 220 nm.

One microbial isolate, I 24, originating from a Stonewall Merck facility sludge sample was found to accumulate large amounts of trans 1R,2R indandiol with an enantiomeric excess greater that 99%. After proper scale up, isolation of the trans-indandiol was performed.

EXAMPLE 2

Purification and isolation of trans-indandiol

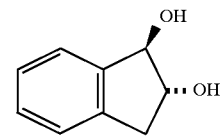

The bioconversion of indene was repeated, employing a 2-liter shake flask containing 150 ml of cultivation medium HL. Cultivation medium HL contains (per liter of water): corn steep liquor, 25 g; molasses, 25 g; yeast extract, 2 g, 0.5 g; $MgSO_4.7H_2O$, 1 g; NaCl, 5 g; $CaCO_3$, 2.5 g. A volume of 30 ml of sterile silicone oil and 900 μl of indene were added to the flask. A volume of 10 ml of a 48-hour old seed culture (in tryptic soy broth) was used to inoculate the flask. Daily additions of 10 ml of sterile molasses and of 900 μl of indene were made to the flask. Also, after 96 hours of cultivation, 3 ml of solution B and 2 ml of trace element solution A9 were added to the flask. Solution B contained (per liter of water): $MgSO_4.7H_2O$, 20 g; $FeSO_4.7H_2O$, 2 g. The composition of solution A9 is described in example 1. The flask was incubated at 28° C. on a shaker top operated at 220 rpm. A trans indandiol concentration of about 1.8 g/l was reached after about 216 hours of cultivation. The content of the flask was centrifuged and the water layer was separated from the silicone oil layer and from the cell pellet. The water layer, containing the trans indandiol was loaded onto a 150 ml column containing about 120 ml of nonionic macroporous polymeric resin. The materials were eluted from the column, using a step gradient of methanol in water (from 0% to 100% methanol). The fractions were collected and analyzed by HPLC, and those containing the trans indandiol were pooled and dried under a stream of nitrogen. The resulting material was analyzed by NMR. It was 94.5% ee. NMR: δH 7.26 (m, 1H), 7.21–7.12 (om, 3H), 5.40 (s, 1H), 5.19 (s, 1H), 4.69 (d, J=4.3, 1H), 4.07 (m, 1H), 3.07 (dd, J=15.5, 7.1, 1H), 2.59 (dd, J=15.5, 7.0 1H). δC 144.1, 139.4, 127.5, 126.4, 124.5, 124.2, 80.6, 80.0, 38.0.

$^{13}C$ NMR: 144.1149, 139.4077, 127.5151 126.4425, 124.5421, 124.2072 80.5777, 79.9808, 38.0234

EXAMPLE 3

Further Purification

A. Centrifugation of whole broth and extraction of the aqueous layer with isopropyl acetate

One liter of whole fermentation broth was centrifuged. The uppermost oil layer (210 mL), the solids (29 g) and the interfacial material (90 g) were discarded. 680 mL aqueous material, which contained 92% of the product, was recovered. The 680 mL aqueous layer was then extracted in two stages with an equivalent volume of isopropyl acetate (IPOAc). The recovery of product in the two IPOAc extracts was 50%.

| Sample | concentration | volume | total amount |
|---|---|---|---|
| whole fermentation broth | 1.21 g/L | 1 liter | 1.21 g |
| oil layer | 0 | 210 mL | 0 |
| interfacial layer | 0.96 g/L | 90 g | 0.09 g |
| aqueous layer | 1.64 g/L | 680 mL | 1.11 g |
| first IPOAc extract of aqueous layer | 0.73 g/L | 470 mL | 0.34 g |
| second IPOAc extract of aqueous layer | 0.56 g/L | 395 mL | 0.22 g |

B. Concentration

The two extracts prepared above were pooled with similar extracts and were concentrated. The final volume was 150 mL.

C. Crystallization

The entire concentrate was transferred to a 500 mL round bottom flask and placed in a chilled water bath at 25° C. and stirred continuously while the bath was chilled from 25° C. to 10° C. over a period of six hours, then held at 10° C. for an additional ten hours. The crystals were collected on a fine mesh 15 mL scintered glass funnel and washed with 10 mL cold IPOAc. The washed crystals were dried at ambient temperature for 24 hours in a vacuum oven.

EXAMPLE 4

A. Conversion of Trans-1R,2R-Indandiol to Cis-1S-Amino-2R-Indanol

| Materials | Experimental Amount | MW | Moles |
|---|---|---|---|
| Cis-1S,2R-indandiol | 100 g | 150.18 | 0.66 |
| 20% oleum (sulfuric acid/sulfur trioxide) | 66.2 mL | 98.08 | 1.33 |
| Acetonitrile | 633.3 mL | | |
| Water | 1000 mL | | |

Trans-1R,2R-Indandiol (100 g, 0.66 mole) is added to acetonitrile (633 mL) at 25° C. then cooled to −25° to −30° C. A solution of 20% oleum (66.2 mL, 1.33 mole) is added, while maintaining the temperature below −10° C. After the addition is completed, the mixture is warmed to 20° C., aged for 1.5 h, then water is added (1000 mL). The acetonitrile solvent is distilled until the internal temperature reached approximately 100° C. The mixture is aged at this temperature for 4.5 h. The solution is concentrated to 100 g of amino-indanol/L.

B. Isolation of (−) Cis-Aminoindanol Using Reverse Ion Pairing Extractive Workup of the Ritter Solution Starting From Diol

| Materials | Amount | MW | Moles |
|---|---|---|---|
| Step A Product | 548.7 g (50.0 g) cis-aminoindanol | 149.2 | 0.335 |
| 1-butanol | 501 mL | | |
| 50% NaOH | 145 mL | 40 | |
| Water | 625 mL | | |
| L-tartaric acid | 60.0 g | 150.1 | 0.4 |

Into a 2 liter round-bottom flask equipped with a thermometer and over-head stirrer is placed 548.7 g of solution from the Ritter (50.0 g cis-aminoindanol from Step A) and 167 mL of 1-butanol. The addition of 50% NaOH is started while maintaining temperature below 40° C. with a water bath. This addition is continued until the pH was greater than 12. A total of 103 mL of 50% NaOH is added. The mixture darkened during the addition.

The mixture is placed in a separatory funnel, and the layers separated. The aqueous layer is then extracted with 2×167 mL 1-butanol. The three organic layers are combined and extracted with a solution of 60.0 g L-tartaric acid (1.2 mole equivalents) in 250 mL of water. The layers are separated and the organic layer is further extracted with 3×125 mL of water. The combined aqueous layer is then concentrated under vacuum to 220 mL.

The concentrate is rinsed into a 500 mL round-bottom flask equipped with a thermometer and over-head stirrer with 30 ML of water. The addition of 50% NaOH is then started. During the addition, the temperature is maintained below 45° C. with a water batch. The cis-aminoindanol starts to crystallize between pH 8 and 9. The addition is continued until the pH is greater than 12. A total of 42 mL of 50% NaOH is added. The mixture is slowly cooled to 0–°5 ° C., and aged for 2 hours, filtered and washed with 150 mL of 0–°5 ° C. water. Dry in a vacuum oven with a nitrogen purge at 45° C. for 18 hours.

C. Isolation of (−)-Cis-Aminoindanol Using A Dowex 50×8 Resin Column Workup of the Ritter Solution Starting From Diol

| Materials | Experimental Amount | MW | Moles |
|---|---|---|---|
| Step A Product | 550 mL (50.0 g) cis-aminoindanol | 149.2 | 0.335 |
| Dowex 50 × 8 (100 mesh) resin | 500 mL (in water) | | |
| 50% NaOH | 34.5 g | 40 | |
| Water | 600 | | |
| 20% MeCN in water | 2175 | | |

A 500 mL Dowex 50×8 (100 mesh) resin column is set up. The column is washed, then back washed with water. The diol Ritter solution (50.0 g cis-aminoindanol in 550 mL Product of Step A) is loaded onto the column with a flow rate of 1.5 bed volumes per hour. The column is then washed with 600 mL of water. There is less than 1% breakthrough.

At first, the elution is tried using NaCl but this is not efficient. A total of 12.3 g of cis-aminoindanol is recovered. The column is washed with 500 mL of 20% MeCN in water followed by the elution with NaOH below.

Dissolve 20.3 g of 50% NaOH in 250 mL of 20% MeCN in water. Pump the solution up flow onto the column. Follow with a 100 mL 20% MeCN line rinse. Let stand for 1.75 hours. Start eluting the column with a 1.5–2 bed volume flow rate. When the solvent reaches the resin bed, elute with 750 mL of 20% MeCN in water.

Dissolve 11.5 g of 50% NaOH in 250 mL of 20% MeCN in water. Pump the solution up flow onto the column. Follow with a 100 mL 20% MeCN line rinse. Let stand for 1.75 hours. Start eluting the column with a 1.5–2 bed volume flow rate. When the solvent reaches the resin bed, elute with 750 mL of 20% MeCN in water.

Dissolve 2.7 g of 50% NaOH in 250 mL of 20% MeCN in water. Pump the solution onto the column. Start eluting the column with a 1.5–2 bed volume flow rate. When the solvent reaches the resin bed, elute with 500 mL of 20% MeCN in water.

The pH of the combined eluents from the first two elutions is adjusted to 2.95 with concentrated HCl. The solution is then concentrated to 228 mL under vacuum. This solution is then used in various crystallization experiments.

EXAMPLE 5

Preparation of Amide 9

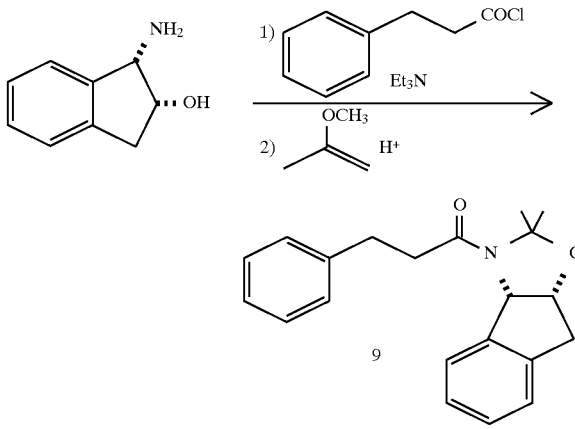

A solution of (−)-cis-1-aminoindan-2-ol (884 g, 5.93 mol) in 17.8 L of dry THF (KF=55 mg/mL) (KF stands for Karl Fisher titration for water) and triethylamine (868 mL, 6.22 mol) in a 50 L round bottom flask equipped with a thermocouple probe, mechanical stirrer, and a nitrogen inlet adapter and bubbler, was cooled to 15° C. Then, 3-phenylpropionyl chloride (1000 g, 5.93 mol) was added over 75 minutes, while the internal temperature between 14–24° C. with an ice-water cooling batch. After addition, the mixture was aged at 18° to 20° C. for 30 minutes and checked by HPLC analysis for the disappearance of (−)-cis-1-aminoindan-2-ol.

Progress of the reaction is monitored by high performance liquid chromatography (HPLC) analysis: 25 cm Dupont C8-RX column, 60:40 acetonitrile/10 mM ($KH_2PO_4$/ $K_2HPO_4$), 1.0 mL/min., injection volume=20 mL, detection=200 nm, sample preparation=500×dilution. Approximate retention times:

| retention time (min) | identity |
|---|---|
| 6.3 | cis-aminoindanol |

The reaction was treated with pyridinium p-toluene-sulfonate (241 g, 0.96 mol, 0.16 equiv.) and stirred for 10 minutes (the pH of the mixture after diluting 1 mL sample with an equal volume of water is between 4.3–4.6). Then, 2-methoxypropene (1.27 L, 13.24 mol, 2.2 equiv.) was added and reaction was heated to 38°–40° C. for 2 h. The reaction mixture was cooled to 20° C. and partitioned with ethyl acetate (12 L) and 5% aqueous $NaHCO_3$ (10 L). The mixture was agitated and the layers were separated. The ethyl acetate extract was washed with 5% aqueous $NaHCO_3$ (10 L) and water (4 L). The ethyl acetate extract was dried by atmospheric distillation and solvent switched to cyclohexane (total volume of ~30 L). At the end of the distillation and concentration (20 volume % of ethyl acetate extraction volume), the hot cyclohexane solution was allowed to slowly cool to 25° C. to crystallize the product. The resulting slurry was further cooled to 10° C. and aged for 1 h. The product was isolated by filtration and the wet cake was washed with cold (10° C.) cyclohexane (2×800 mL). The washed cake was dried under vacuum (26" of Hg) at 40° C. to afford 1.65 kg of acetonide 9 (86.4%, 98 area % by HPLC). $^1$H NMR (300.13 MHz, $CDCl_3$, major rotamer) d 7.36–7.14 (m, 9H), 5.03 (d, J=4.4, 1H), 4.66 (m, 1H), 3.15 (m, 2H), 3.06 (br s, 2H), 2.97 (m, 2H), 1.62 (s, 3H), 1.37 (s, 3H); $^{13}$C NMR (75.5 MHz, $CDCl_3$, major rotamer) $d_c$ 168.8, 140.9, 140.8, 140.6, 128.6, 128.5, 128.4, 127.1, 126.3, 125.8, 124.1, 96.5, 78.6, 65.9, 38.4, 36.2, 31.9, 26.5, 24.1.

Analysis calculated for $C_{21}H_{23}NO_2$: C, 78.47;H, 7.21; N, 4.36. Found: C, 78.65;H, 7.24; N, 4.40.

EXAMPLE 6

Preparation of Epoxide 11 Tosylate Method

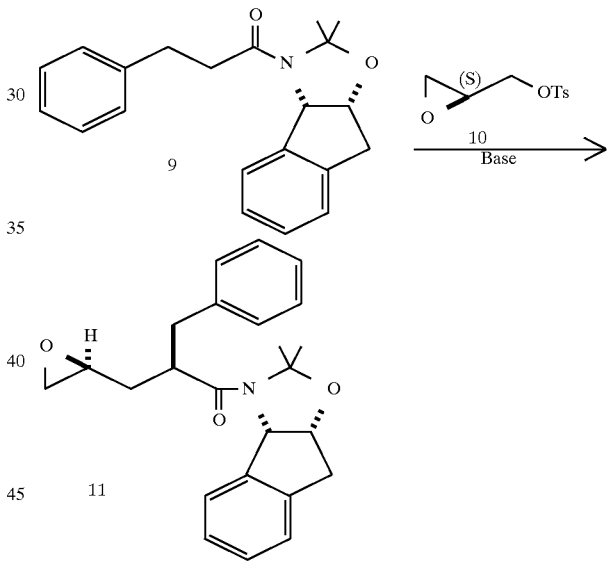

A solution of acetonide 9 (1000 g, 3.11 mol) and 2(S)-glycidyl tosylate 10 (853 g, 3.74 mol, 1.2 equiv.) in 15.6 L of THF (KF=22 mg/mL) in a 50 L 4-neck round bottom flask, equipped with a thermocouple, mechanical stirrer, addition funnel and nitrogen inlet adapter was degassed 3 times via vacuum-nitrogen purge and cooled to −56° C. Then, lithium hexamethyldisilazide ($LiN[(CH_3)_3Si]_2$)(2.6 L, 1.38M, 1.15 equiv.) was added over 2 h, while keeping the internal temperature between −50° to −45° C. The reaction mixture was stirred at −45° to −40° C. for 1 h and then allowed to warm to −25° C. over 1 h. The mixture is stirred between −25° to −22° C. for 4 h (or until the starting acetonide is 3.0 area %).

Progress of the reaction is monitored by HPLC analysis: 25 cm×4.6 nm Zorbax Silica column, 20% ethyl acetate in hexane, 2.0 mL/min, injection volume=20 mL, detection=254 nm, sample preparation=100×dilution. Approximate retention times:

| retention time (min) | identity |
| --- | --- |
| 5.5 | amide 9 |
| 6.5 | glycidyl tosylate 10 |
| 13.5 | epoxide 11 |

The reaction mixture was quenched with DI water (6.7 L) at −15° C. and partitioned with ethyl acetate (10 L). The mixture was agitated and the layers were separated. The ethyl acetate extract was washed with a mixture of 1% aqueous NaHCO₃ (5 L) and saturated NaCl (0.5 L). The ethyl acetate extract (28.3 L) was concentrated by vacuum distillation (28" of Hg) and additional ethyl acetate was added to complete the solvent switch to ethyl acetate (final volume=11.7 L). The ethyl acetate concentrate was further solvent switched to MeOH to crystallize the product and concentrated to a final volume of 3.2 L. The residual ethyl acetate solvent was removed by charging 10 L of methanol and collecting 10 L of distillate. The resulting slurry was stirred at 22° C. for 1 h, then cooled to 5° C. and aged for 0.5 h. The product was isolated by filtration and the wet cake was washed with cold methanol (2×250 mL). The washed cake was dried under vacuum (26" of Hg) at 25° C. to afford 727 g of epoxide 11 (61.2%, 98.7 area % of the major epoxide by HPLC). $^{13}$C NMR (300 MHz, CDCl₃) d 171.1, 140.6, 140.5, 139.6, 129.6, 128.8, 128.2, 127.2, 126.8, 125.6, 124.1, 96.8, 79.2, 65.8, 50.0, 48.0, 44.8, 39.2, 37.4, 36.2, 26.6, 24.1.

EXAMPLE 7

Preparation of penultimate 14

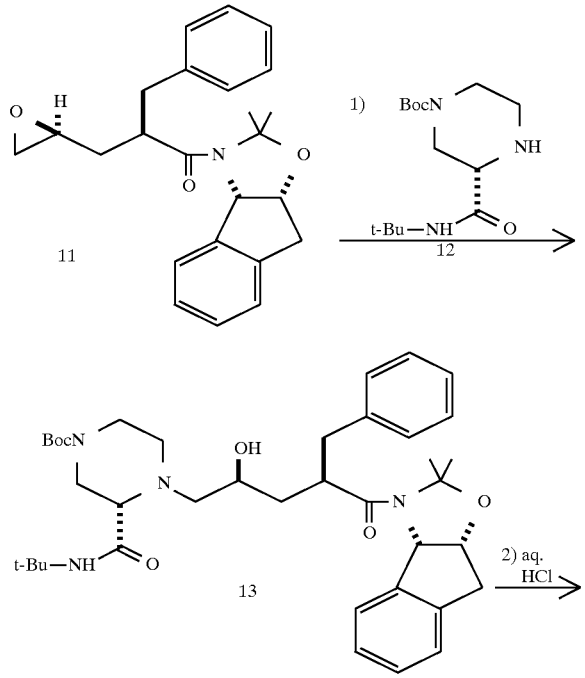

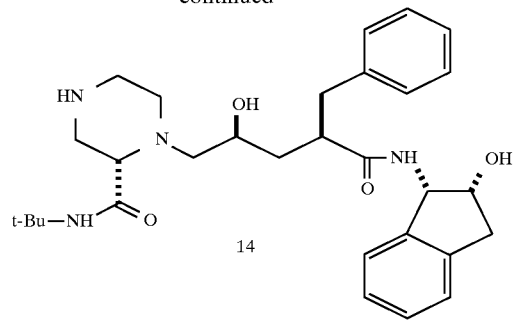

A slurry of the 2(S)-t-butylcarboxamide-4-N-Boc-piperazine 12 (1950 g, 6.83 mol, >99.5% ee) (ee= stereoisomeric excess) and the epoxide 11 (2456 g, 97.5:2.5 mixture of 4 S/R epoxides, 6.51 mol) in isopropanol (2-propanol, 18.6 L) in a 72 L round bottom flask with four inlets, equipped with a mechanical stirrer, reflux condenser, steam bath, Teflon coated thermocouple and nitrogen inlet, was heated to reflux (internal temperature was 84–°85° C.). After 40 min, a homogeneous solution was obtained. The mixture was heated at reflux for 28 h.

The internal temperature during reflux was 84–°85° C. Progress of the reaction was monitored by HPLC analysis: 25 cm Dupont C8-RX column, 60:40 acetonitrile/10 mM (KH₂PO₄/K₂HPO₄), 1.0 mL/min., detection=220 nm, sample preparation=2 mL, reaction mixture diluted to 1 mL in acetonitrile. Approximate retention times:

| retention time (min) | identity |
| --- | --- |
| 4.8 | piperazine 12 |
| 8.9 | epoxide 11 |
| 15.2 | coupled product 13 |

After 28 h, the remaining epoxide 11 and coupled product 13 (by HPLC analysis) were 1.5 area % and 91–93 area %, respectively. The mixture was cooled to 0° to 5° C. and 20.9 L of 6 N HCl was added while keeping the temperature below 15° C. After the addition was complete, the mixture was warmed to 22° C. Evolution of gas is noted at this point (isobutylene). The mixture was aged at 20° to 22° C. for 6 h.

Progress of the reaction was monitored by HPLC analysis: same conditions as above. Approximate retention times:

| retention time (min) | identity |
| --- | --- |
| 7.0 | cis-aminoindanol |
| 11.9 | penultimate 14 |
| 15.1 | coupled product 13 |

The mixture was cooled to 0° C. and 7.5 L of 50% NaOH was slowly added to adjust the pH of the mixture to pH=11.6, while keeping the temperature less than 25° C. during the addition. The mixture was partitioned with ethyl acetate (40 L) and water (3 L). The mixture was agitated and the layers were separated. The organic phase (60 L) was concentrated under reduced pressure (29" of Hg) and solvent switched to DMF and concentrated to a final volume of 10.5 L (KF=1.8 mg/mL). The HPLC assay yield of 14 in ethyl acetate was 86.5%. The penultimate compound 14 in DMF was directly used in the next step without further purification. For isolated 14: $^{13}$C NMR (75.4 MHz, CDCl₃) d 175.2, 170.5, 140.8, 140.5, 139.9, 129.1, 128.5, 127.9, 126.8, 126.5, 125.2, 124.2, 73.0, 66.0, 64.8, 62.2, 57.5, 49.5, 47.9, 46.4, 45.3, 39.6, 39.3, 38.2, 28.9.

EXAMPLE 8
Preparation of monohydrate of Compound J

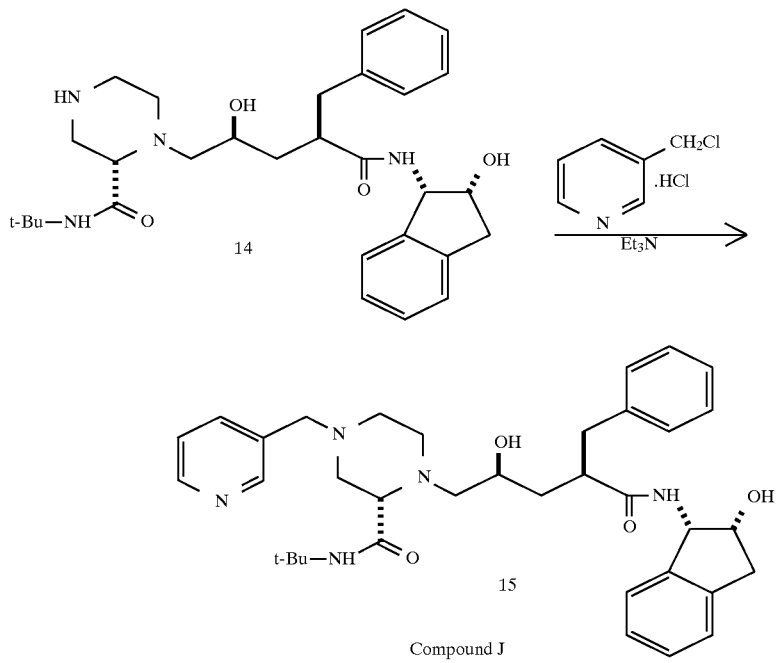

Compound J

The solution of 14 in DMF (10.5 L, KF=10 mg/mL) from the previous step was charged with 8 L of sieve dried DMF (KF<30 mg/L) and the mixture was heated with a steam bath under vacuum of 30" of Hg to distill off mainly water and/or any residual isopropanol or ethyl acetate solvent. The final concentrate volume was 13.5 L (KF=1.8 mg/mL) and then triethylamine (2.86 L, 20.51 mol) was added to the 25° C. solution followed by 3-picolyl chloride hydrochloride (96%, 1287 g, 7.84 mol). The resulting slurry was heated to 68° C.

The progress of the reaction was followed by HPLC analysis using the same conditions as the previous step. Approximate retention times:

| Retention time (min) | Identity |
|---|---|
| 2.7 | DMF |
| 4.2 | 3-picolyl chloride |
| 4.8 | Compound J |
| 9.1 | penultimate 14 |

The mixture was aged at 68° C. until the residual penultimate compound 14 was <0.3 area % by HPLC analysis.

The mixture was stirred at 68° C. for 4 h, then cooled to 25° C. and partitioned with ethyl acetate (80 L) and a mixture of 24 L of saturated aqueous $NaHCO_3$ and distilled water (14 L). The mixture was agitated at 55° C. and the layers were separated. The ethyl acetate layer was washed three times with water (20 L) at 55° C. The washed ethyl acetate layer is concentrated at atmospheric pressure to a final pot volume of 30 L. At the end of the atmospheric concentration, water (560 mL) was added to the hot solution and the mixture was cooled to 55° C. and seeded with Compound J monohydrate. The mixture was cooled to 4° C. and filtered to collect the product. The product was washed with cold ethyl acetate (2×3 L), and dried at house vacuum at 25° C. to afford 2905 g (70.7%) of Compound J monohydrate as a white solid.

EXAMPLE 9
Pyrazine-2-tert-butyl carboxamide 17

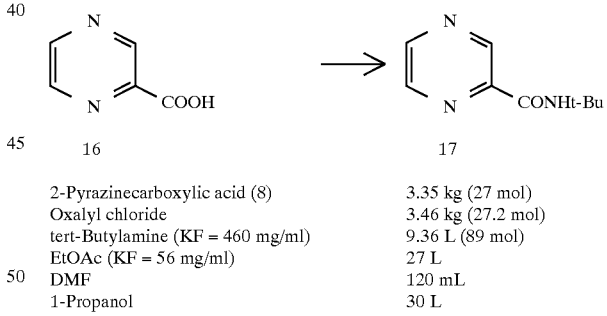

| | |
|---|---|
| 2-Pyrazinecarboxylic acid (8) | 3.35 kg (27 mol) |
| Oxalyl chloride | 3.46 kg (27.2 mol) |
| tert-Butylamine (KF = 460 mg/ml) | 9.36 L (89 mol) |
| EtOAc (KF = 56 mg/ml) | 27 L |
| DMF | 120 mL |
| 1-Propanol | 30 L |

The carboxylic acid 16 was suspended in 27 L of EtOAc and 120 mL of DMF in a 72 L 3-neck flask with mechanical stirring under $N_2$ and the suspension was cooled to 2° C. The oxalyl chloride was added, maintaining the temperature between 5° and 8° C.

The addition was completed in 5 h. During the exothermic addition CO and $CO_2$ were evolved. The HCl that was formed remained largely in solution. A precipitate was present which is probably the HCL salt of the pyrazine acid chloride. Assay of the acid chloride formation was carried out by quenching an anhydrous sample of the reaction with t-butylamine. At completion <0.7% of acid 16 remained.

The assay for completion of the acid chloride formation is important because incomplete reaction leads to formation of a bis-tert-butyl oxamide impurity.

The reaction can be monitored by HPLC: 25 cm Dupont Zorbax RXC8 column with 1 mL/min flow and detection at 250 nm;

linear gradient from 98% of 0.1% aqueous $H_3PO_4$ and 2% $CH_3CN$ to 50% aqueous $H_3PO_4$ and 50% $CH_3CN$ at 30 min. Retention times: acid 16=10.7 min, amide 17=28.1 min.

The reaction mixture was aged at 5° C. for 1 h. The resulting slurry was cooled to 0° C. and the tert-butylamine was added at such a rate as to keep the internal temperature below 20° C.

The addition required 6 h, as the reaction was very exothermic. A small portion of the generated tert-butylammonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% $NaHCO_3$ and 2×2 L of saturated aq. NaCl. The organic phase was treated with 200 g of Darco G60 carbon and filtered through Solka Flok and the cake was washed with 4 L of EtOAc.

Carbon treatment efficiently removed some purple color in the product.

The EtOAc solution of 17 was concentrated at 10 mbar to 25% of the original volume. 30 L of 1-propanol were added, and the distillation was continued until a final volume of 20 L was reached.

At this point, the EtOAc was below the limit of detection in the $^1H$ NMR (<1%). The internal temperature in this solvent change was <30° C. A 1-propanol/EtOAC solution of 3 was stable to reflux atmospheric pressure for several days.

Evaporation of an aliquot gave a tan solid m.p. 87°–88° C. $^{13}C$ NMR (75 MHz, $CDCl_3$, ppm) 161.8, 146.8, 145.0, 143.8, 142.1, 51.0, 28.5.

EXAMPLE 10 rac-2-tert-Butyl-carboxamide-piperazine 18

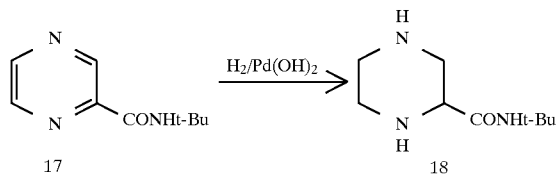

Materials

Pyrazine-2-tert-butylcarboxamide 17 2.4 kg (13.4 mol) in 1-Propanol solution 12 L 20% $Pd(OH)_2/C$ 16 wt. % water 144 g.

The pyrazine-2-tert-butylcarboxamide 17/1-propanol solution was placed into the 5 gal autoclave. The catalyst was added and the mixture was hydrogenated at 65° C. at 40 psi (3 atm) of $H_2$.

After 24 h the reaction had taken up the theoretical amount of hydrogen and GC indicated <1% of 17. The mixture was cooled, purged with $N_2$ and the catalyst was removed by filtration through Solka Floc. The catalyst was washed with 2 L of warm 1-propanol.

It was found that the use of warm 1-propanol during washing of the filter cake improved filtration and lowered the losses of product on the filter cake.

The reaction was monitored by GC: 30 m Megabore column, from 100° C. to 160° C. at 10° C./min, hold 5 min, then at 10° C./min to 250° C., retention times: 17=7.0 min, 18=9.4 min. The reaction could also be monitored by TLC with EtOAc/MeOH (50:50) as solvent and Ninhydrin as developing agent.

Evaporation of an aliquot indicated that the yield over amidation and hydrogenation is 88% and that the concentration of 18 is 133g/L.

Evaporation of an aliquot gave 18 as a white solid m.p. 150°–151° C.; $^{13}C$ NMR (75 MHz, $D_2O$, ppm) 173.5, 59.8, 52.0, 48.7, 45.0, 44.8, 28.7.

EXAMPLE 11

(S)-2-tert-Butyl-carboxamide-piperazine bis (S)-Camphorsulfonic acid salt (S)-19

Materials

| | |
|---|---|
| rac-2-tert-Butyl-carboxamide-piperazine 18 | 4.10 kg (22.12 mol) |
| in 1-Propanol Solution | in 25.5 Kg solvent |
| (S)-(+)-10-Camphorsulfonic acid | 10.0 Kg (43.2 mol) |
| 1-Propanol | 12 L |
| Acetonitrile | 39 L |
| Water | 2.4 L |

The solution of amine 18 in 1-propanol was charged to a 100 L flask with an attached batch concentrator. The solution was concentrated at 10 mbar and a temperature <25° C. to a volume of ca 12 L.

At this point the product had precipitated from the solution, but went back into a solution when the mixture was heated to 50° C.

Analysis of a homogeneous aliquot indicated that the concentration of 18 was 341 g/L. The concentration was determined by HPLC: 25 cm Dupont Zorbax RXC8 column with 1.5 mL/min flow and detection at 210 nm, isocratic (98/2) $CH_3CN$/0.1% aqueous $H_3PO_4$. Retention time of 18:2.5 min.

Acetonitrile (39 L) and water (2.4 L) were added to give a clear, slightly brown solution.

Determination of the water content by KF titration and $CH_3CN$/1-propanol ratio by $^1H$ NMR integration showed that the $CH_3CN$/1-propanol/$H_2O$ ratio was 26/8/1.6. The concentration in the solution was 72.2 g/L.

The (S)-10-camphorsulfonic acid was charged over 30 min in 4 portions at 20° C. The temperature rose to 40° C. after the CSA was added. After a few minutes a thick white precipitate formed. The white slurry was heated to 76° C. to dissolve all the solids, the slightly brown solution was then allowed to cool to 21° C. over 8 h.

The product precipitated at 62° C. The product was filtered without aging at 21° C., and the filter cake was washed with 5 L of the $CH_3CN$/1-propanol/$H_2O$ 26/8/1.6 solvent mixture. It was dried at 35° C. in the vacuum oven with $N_2$ bleed to give 5.6 Kg (39%) of 19 as a white crystalline solid m.p. 288°–290° C. (with decomp.) $[\alpha]D^{25}$= 18.9° (c=0.37, $H_2O$). $^{13}C$ NMR (75 MHz, $D_2O$, ppm) 222.0, 164.0, 59.3, 54.9, 53.3, 49.0, 48.1, 43.6, 43.5, 43.1, 40.6, 40.4, 28.5, 27.2, 25.4, 19.9, 19.8.

The ee of the material was 95% according to the following chiral HPLC assay: an aliquot of 19 (33 mg) was suspended in 4 mL of EtOH and 1 mL of Et₃N. Boc₂O (11 mg) was added and the reaction mixture was allowed to age for 1 h. The solvent was completely removed in vacuo, and the residue was dissolved in ca. 1 mL of EtOAc and filtered through a Pasteur pipet with $SiO_2$, using EtOAc as eluent. The evaporated product fractions were redissolved in hexanes at ca. 1 mg/mL. The stereoisomers were separated on a Daicel Chiracell AS column with a hexane/IPA (97:3) solvent system at a flow rate of 1 mL/min and detection at 228 nm. Retention times: S antipode=7.4 min, R=9.7 min.

EXAMPLE 12

(S)-2-tert-Butylcarboxamide-4-tert-butoxycarbonyl-piperazine 12 from salt 19

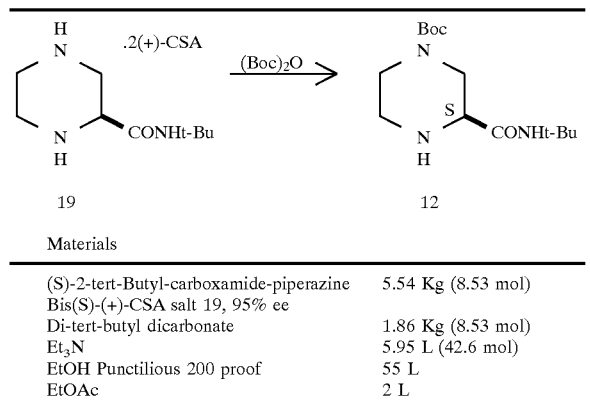

Materials

| | |
|---|---|
| (S)-2-tert-Butyl-carboxamide-piperazine Bis(S)-(+)-CSA salt 19, 95% ee | 5.54 Kg (8.53 mol) |
| Di-tert-butyl dicarbonate | 1.86 Kg (8.53 mol) |
| Et₃N | 5.95 L (42.6 mol) |
| EtOH Punctilious 200 proof | 55 L |
| EtOAc | 2 L |

To the (S)-CSA salt 19 in a 100 L 3-neck flask with an addition funnel under N₂ was added EtOH, followed by triethylamine at 25° C. The solid dissolved readily on the addition of the Et3N. The Boc₂O was dissolved in EtOAc and charged to the addition funnel. The solution of Boc₂O in EtOAc was added at such a rate as to keep the temperature below 25° C. The addition took 3 h. The reaction mixture was aged for 1 h after completion of the addition of the Boc₂O solution.

The reaction can be monitored by HPLC:25 cm Dupont Zorbax RXC8 column with 1 mL/min flow and detection at 228 nm, isocratic (50/50) $CH_3CN/0.1M\ KH_2PO_4$ adjusted to pH=6.8 with NaOH. Retention time of 12=7.2 min. The chiral assay was carried out using the same system as in the previous step. The reaction could also be monitored by TLC with a 100% EtOAc as the solvent. ($R_f$=0.7)

The solution was then concentrated to ca. 10 L at an internal temperature of <20° C. in a batch-type concentrator under 10 mbar vacuum. The solvent switch was completed by slowly bleeding in 20 L of EtOAc and reconcentrating to ca 10 L. The reaction mixture was washed into an extractor with 60 L of EtOAc. The organic phase was washed with 16 L of 5% aqueous $Na_2CO_3$ solution, 2×10 L Di water and 2×6 L of saturated aqueous sodium chloride. The combined aqueous washes were back extracted with 20 L of EtOAc and the organic phase was washed with 2×3 L water and 2×4 L of saturated aqueous sodium chloride. The combined EtOAc extracts were concentrated under 10 mbar vacuum with an internal temperature of <20° C. in a 100 L batch-type concentrator to ca. 8 L. The solvent switch to cyclohexane was achieved by slowly bleeding in ca. 20 L of cyclohexane, and reconcentrating to ca. 8 L. To the slurry was added 5 L of cyclohexane and 280 mL of EtOAc and the mixture was heated to reflux, when everything went into solution. The solution was cooled and seed (10 g) was added at 58° C. The slurry was cooled to 22° C. in 4 h and the product was isolated by filtration after a 1 h age at 22° C. The filter cake was washed with 1.8 L of cyclohexane and dried in the vacuum oven at 35° C. under N₂ bleed to give 1.87 Kg (77%, >99.9 area % by HPLC, R-isomer below level of detection) of 12 as a slightly tan powder. $[a]D^{25}=22.0°$ (c=0.20, MeOH), m.p. 107° C.; $^{13}C$ NMR (75 MHz, CDCl₃, ppm) 170.1, 154.5, 79.8, 58.7, 50.6, 46.6, 43.6, 43.4, 28.6, 28.3.

EXAMPLE 13

Preparation of racemic indene oxide

Indene (95%, 122 mL) was dissolved in methanol (812 mL) and acetonitrile (348 mL), then filtered. The filtrate was diluted with 0.05M sodium dibasic phosphate (116 mL), then adjusted to pH 10.5 with 1M aqueous sodium hydroxide. Aqueous hydrogen peroxide (35%, 105 mL) was diluted with water (53 mL) and added over 3 h, while maintaining the temperature at 25° C. and the internal pH at 10.5 with 1M aqueous sodium hydroxide (120 mL total).

After 6 h, 1M aqueous sodium metabisulfite was added (26 mL), while maintaining the pH above 8.3 by addition of 1M aqueous NaOH (39 mL). Water (700 mL) was added and the mixture extracted with methylene chloride (580 mL and 300 mL). The combined organic extracts containing indene oxide (117 g) were concentrated to a volume of 600 mL.

EXAMPLE 14

Assay for Inhibition of Microbial Expressed HIV Protease

Inhibition studies of the reaction of the protease expressed in *Eschericia coli* with a peptide substrate [Val-Ser-Gln-Asn-(betanapthyl)Ala-Pro-Ile-Val, 0.5 mg/mL at the time the reaction is initiated] were in 50 mM Na acetate, pH 5.5, at 30° C. for 1 hour. Various concentrations of inhibitor in 1.0 ul DMSO were added to 25 ul of the peptide solution in water. The reaction is initiated by the addition of 15 ul of 0.33 nM protease (0.11 ng) in a solution of 0.133M Na acetate pH 5.5 and 0.1% bovine serum albumin. The reaction was quenched with 160 μul of 5% phosphoric acid. Products of the reaction were separated by HPLC (VYDAC wide pore 5 cm C-18 reverse phase, acetonitrile gradient, 0.1% phosphoric acid). The extent of inhibition of the reaction was determined from the peak heights of the products. HPLC of the products, independently synthesized, proved quantitation standards and confirmation of the product composition. Compound J gave $IC_{50}$ of about 0.6 nM.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A process for synthesizing (1R,2R)-indandiol which comprises incubating a mixture comprising indene and Rhodococcus sp. MA7205 (I24), ATCC 55805 to give (1R,2R)-indandiol.

2. The process according to claim 1, which further comprises recovering the (1R,2R)-indandiol from the incubation mixture.

3. The process according to claim 2, wherein said recovering comprises purifying the (1R,2R)-indandiol by crystallization to obtain (1R,2R)-indandiol substantially free of any stereoisomer.

4. A process for synthesizing (1S)-amino-(2R)-indanol substantially free of any stereoisomer which comprises:

(A) incubating a first mixture comprising indene and Rhodococcus sp. MA7205 (I 24), ATCC 55805 to give (1R,2R)-indandiol;

(B) recovering the (1R,2R)-indandiol wherein said recovering comprises purifying the (1R,2R)-indandiol by crystallization to obtain a (1R,2R)-indandiol substantially free of any stereoisomer;

(C) dissolving one equivalent of the (1R,2R)-indandiol of step (B) in excess acetonitrile to give a second mixture and maintaining the second mixture between about −40° C. and about 25° C.;

(D) mixing thereto excess equivalents of strong acid; and (E) maintaining the reaction at between about −40° C. and about 25° C. to give (1S)-amino-(2R)-indanol substantially free of any stereoisomer.

5. The process according to claim 4, which further comprises (F) subjecting the product of step (E) to reverse ion pair extraction to give substantially pure (1S)-amino-(2R)-indanol.

6. The process according to claim 4, which further comprises (F) subjecting the product of step (E) to cation exchange chromatography to give substantially pure (1S)-amino-(2R)-indanol.

* * * * *